United States Patent
Trivedi et al.

[11] Patent Number: 6,165,447
[45] Date of Patent: Dec. 26, 2000

[54] SYNERGISTIC ANTIBACTERIAL COMBINATION

[75] Inventors: Harsh M. Trivedi, Woodbridge; Susan M. Herles, Flemington; Lori H. Szeles, Old Bridge; Abdul Gaffar, Princeton, all of N.J.

[73] Assignee: Colgate-Palmolive Company, New York, N.Y.

[21] Appl. No.: 09/333,543

[22] Filed: Jun. 15, 1999

[51] Int. Cl.[7] .............................. A61K 7/16; A61K 31/12; A61K 7/26
[52] U.S. Cl. ............................. 424/49; 424/58; 424/405; 514/690
[58] Field of Search ................... 424/49–58, 405; 514/690

[56] References Cited

U.S. PATENT DOCUMENTS

| | | | |
|---|---|---|---|
| 3,932,603 | 1/1976 | Haas | 424/49 |
| 4,644,084 | 2/1987 | Cowles et al. | 568/341 |
| 4,894,220 | 1/1990 | Nabi et al. | 424/52 |
| 4,918,240 | 4/1990 | Todd et al. | 568/366 |
| 5,082,975 | 1/1992 | Todd et al. | 568/315 |
| 5,166,449 | 11/1992 | Todd et al. | 568/377 |
| 5,334,375 | 8/1994 | Nabi et al. | 424/52 |
| 5,370,863 | 12/1994 | Barney et al. | 424/49 |
| 5,455,038 | 10/1995 | Barney et al. | 424/405 |
| 5,690,911 | 11/1997 | Mirajkar et al. | 424/49 |
| 5,800,803 | 9/1998 | Mirajkar et al. | 424/54 |
| 5,827,895 | 10/1998 | Nutter et al. | 514/690 |

OTHER PUBLICATIONS

Stephan et al J. Antimicrob. Chemother. 42(4): 519–522, 1998.
Tagashira et al Bioscience Biotechnolog Biochemistry 61(2): 332–335, Feb. 1997.
Simpson et al JL. Appl. Bacteriology 72(4): 327–334, Apr. 1992.
Schmalreck et al Can. J. Microbiol. 21(2): 205–212, 1975.
Herles et al J. Dent. Res. 73(11): 1748–1755, 1994
Nabi et al Am. JL. Dentistry 2 Spec. No :197–206, Sep. 1989.

*Primary Examiner*—Shep K. Rose
*Attorney, Agent, or Firm*—Paul Shapiro

[57] ABSTRACT

An antibacterial combination of a nonionic halogenated diphenyl ether compound such as Triclosan and hydrogenated lupulone, the combination being particularly effective in inhibiting the growth of gram-positive bacteria and in the preparation of antiplaque oral compositions.

11 Claims, No Drawings

SYNERGISTIC ANTIBACTERIAL COMBINATION

BACKGROUND OF THE INVENTION

1. Field of the Invention

This invention relates to an synergistic antibacterial combination of a noncationic halogenated hydroxydiphenyl ether and a hydrogenated lupulone derived from beer hops and more particularly to an oral composition containing such combination which exhibits substantially increased antibacterial efficacy against plaque causing oral bacteria.

2. The Prior Art

It is difficult to predict the efficacy of antibacterial agents when incorporated in any delivery vehicle and particularly in oral compositions. For example, dental plaque is a soft deposit which forms on teeth as opposed to calculus which is a hard calcified deposit on teeth. Unlike calculus, plaque may form on any part of the tooth surface, particularly at the gingival margin and is implicated in the occurrence of gingivitis. Cationic antibacterial compounds such as chlorhexidine, benzthonium chloride and cetyl pyridinium chloride have been used by the art as antibacterial antiplaque agents in oral compositions. However, such agents are generally not effective when there is also present in the oral composition an anionic surfactant required for the effective performance of oral compositions such as toothpaste and mouthrinses.

Noncationic antibacterial materials are compatible with anionic surfactants in oral compositions and noncationic halogenated hydroxydiphenyl ethers such as Triclosan have been effectively employed in commercial oral compositions as antibacterial antiplaque agents when mixed with neutral ingredients such as humectants, abrasives and thickeners conventionally used in the formulation of oral compositions. Notwithstanding the antibacterial efficacy of Triclosan, there is a continuing interest in the oral composition field for antibacterial agents which are compatible with anionic surfactants and which improve the efficacy of noncationic halogenated hydroxydiphenyl ethers such as Triclosan.

In addition to Triclosan, beta-acids, also known as lupulones, derived from beer hops, are known to the art to exhibit antibacterial action in oral compositions. For example, U.S. Pat. No. 3,932,603 discloses that hop extract resins, such as lupulone and humulone, are effective as antimicrobials against cariogenic streptococci. U.S. Pat. No. 5,370,863 discloses oral compositions containing hop acids which inhibit gram positive bacteria and plaque formation and periodontal disease.

The beta-acids are also known to inhibit the growth of food pathogens, such as Listeria monocytogenes (U.S. Pat. Nos. 5,286,506; 5,455,038). In addition the hydrogenated form, hexahydrolupulone inhibits the growth of certain Lactobacilli (U.S. Pat. No. 5,082,975). Hydrogenated lupulones appear to be more active and stable than their non-hydrogenated parent compounds. For example, hexahydrocolupulone is believed to be more antibacterial active than colupulone while hexahydrolupulone has been found to be more stable than lupulone. Hexahydrocolupulone can be made by the chemical hydrogenation of colupulone using a number of methods known in the art. For example, hydrogenation can be achieved with platinum (IV) oxide as a catalyst as described by Riedl (Ber. 89:1863 (1956) or by Carson (J. Am. Chem. Soc. 73:1850 (1951). A method for preparing hexahydrolupulone is described in U.S. Pat. No. 5,082,975.

SUMMARY OF THE INVENTION

In accordance with the present invention it has been unexpectedly discovered that a combination of a nonionic halogenated hydroxydiphenyl ether such as Triclosan and a hydrogenated lupulone are synergistically effective in inhibiting the growth of gram-positive bacteria such as A. viscosus. In one embodiment, wherein the combination of an oral antiplaque composition comprising an orally acceptable vehicle and an effective antiplaque amount is present in the combination there is observed enhanced antiplaque activity in substantial excess of the additive antibacterial effect of the individual noncationic halogenated hydroxydiphenyl ether or hydrogenated lupulone. As will hereinafter be demonstrated, hexahydrolupulone and hexahydrocolupulone are particularly effective when used in combination with noncationic halogenated hydroxydiphenyl ethers such as Triclosan.

The fact that halogenated hydroxydiphenyl ether compounds such as Triclosan have been approved as safe and effective for use in a variety of oral care and personal care products and that the hydrogenated lupulones are food grade materials suggests that these compounds will both be suitable as ingredients in daily user oral hygiene products such as dentifrice and mouth rinse formulations as well as in personal care products such as ointments, creams or lotions.

DETAILED DESCRIPTION OF THE PREFERRED EMBODIMENTS

The term "hydrogenated lupulone" includes within its meaning hydrogenated lupulones, derivatives and analogs thereof as well as pharmaceutically acceptable salts thereof. Hexahydrolupulone and hexahydrocolupulone are lupulones preferred in the practice of the present invention.

Typical examples of noncationic halogenated diphenyl ethers which are particularly desirable from considerations of effectiveness, safety and formulation are 2',4,4' trichloro-2-hydroxy-diphenyl ether (Triclosan) and 2,2'-dihydroxy-5,5'-dibromodiphenyl ether.

The antibacterial combination of hydrogenated lupulone and noncationic halogenated diphenyl ether may be administered to the oral cavity or to the skin while dissolved or suspended in a pharmaceutically acceptable vehicle.

When the noncationic halogenated hydroxyphenyl ether and hydrogenated lupulone are used to prepare oral compositions such as dentifrices and mouthrinses each agent is incorporated in the oral composition in a non-toxic, effective antiplaque amount, typically in a range of about 0.003 to about 2%, preferably about 0.02 to about 1% by weight. A mixture of hydrogenated lupulones namely hexahydrolupulone (35% by weight) and hexahydrocolupulone (65% by weight) is available commercial from Haas Hop Products, Washington, D.C.

To further enhance the synergistic antibacterial activity of the antibacterial agent combination of the present invention, an antibacterial enhancing agent may be included in the oral composition. The use of such antibacterial enhancing agents in combination with noncationic antibacterial compounds is known to the art, as for example, U.S. Pat. Nos. 5,188,821 and 5,192,531.

Antibacterial enhancing agents preferred for use in the practice of the present invention include a natural or synthetic anionic polycarboxylates having a molecular weight of about 1,000 to about 5,000,000, preferably about 30,000 to about 500,000. Synthetic anionic polycarboxylates are generally employed in the form of their free acids or preferably partially or more preferably fully neutralized water soluble alkali metal (e.g. potassium and preferably sodium) or ammonium salts. Preferred are 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000, most preferably about 30,000 to about 500,000. These copolymers are available, for example, under the trade designation Gantrez AN 139 (M.W. 500,000), AN 119 (M.W. 250,000); and preferably Gantrez S-97 Pharmaceutical Grade (M.W. 70,000), of GAF Corporation.

Other anionic polycarboxylates useful in the practice of the present invention include the 1:1 copolymers of maleic anhydride with ethyl acrylate, hydroxyethyl methacrylate, N-vinyl-2-pyrollidone, or ethylene, the latter being available, for example, as Monsanto EMA No: 1103, M.W. 10,000 and Grade 61, and 1:1 copolymers of acrylic acid with methyl or hydroxyethyl methacrylate, methyl or ethyl acrylate, isobutyl methacrylate, isobutyl vinyl ether or N-vinyl-2-pyrrolidone.

Additional operative useful polycarboxylate compounds include copolymers of maleic anhydride with styrene, isobutylene or ethyl vinyl either, polyacrylic, polycationic and polymaleic acids, and sulfonacrylic oligomers of M.W. as low as 1,000 available under the trade designation Uniroyal ND-2.

Also useful in the practice of the present invention are the so-called carboxyvinyl polymers, commercially available, for example, under the trade designation Carbopol 934, 940 and 941 from B.F. Goodrich, these polymers consisting of a colloidally water-soluble polymer of polyacrylic acid crosslinked with from about 0.75% to about 2.0% of polyallyl sucrose or polyallyl pentaerythritol as a cross linking agent, often with M.W.'s up to 4–5 million or more.

The antibacterial enhancing agent, when employed in the oral composition, is incorporated in the compositions in weight amounts of about 0.05 to about 5%, preferably about 0.1 to about 3%.

Fluoride ions may also be included in the oral compositions of the present invention to provide an anticaries effect. Among these materials are inorganic fluoride salts, such as soluble alkali metal fluoride salts, for example, sodium fluoride, potassium fluoride, sodium monofluorophosphate and sodium hexafluorosilicate. Alkali metal and tin fluorides, such as sodium and stannous fluorides, sodium monofluorophosphate and mixtures thereof, are preferred.

The amount of fluorine-providing salt is generally present in the oral composition at a concentration of about 0.0005 to about 3.0% by weight. Any suitable minimum amount of such salt may be used, but it is preferable to employ sufficient fluoride salt to release about 300 to 2,000 ppm, more preferably about 800 to about 1,500 ppm, of fluoride ion.

The oral composition of the present invention may be a solution of ingredients such as a mouthrinse or it maybe a semi-solid such as a toothpaste or gel dentifrice or chewing gum or solid lozenge.

In the aspect of this invention wherein the oral composition is a gel or paste, an orally acceptable vehicle, including a water-phase with humectant which is preferably glycerine or sorbitol or an alkylene glycol such as polyethylene glycol or propylene glycol is present, wherein water is present typically in an amount of about 15–40% by weight and glycerine, sorbitol and/or the alkylene glycol (preferably propylene glycol) typically total about 20–75% by weight of the oral composition, more typically about 25–60% by weight.

When the oral composition is substantially semi-solid or pasty in character, such as a toothpaste or gel, the dentifrice vehicle may contain a dentally acceptable abrasive material such as sodium bicarbonate or water insoluble abrasive material such as sodium metaphosphate, potassium metaphosphate, tricalcium phosphate, dihydrated dicalcium phosphate, anhydrous dicalcium phosphate, calcium pyrophosphate, calcium carbonate, aluminum silicate, hydrated alumina, calcined alumina, silica, bentonite, and mixtures thereof.

The abrasive material is generally present in the paste or gel composition in weight concentrations of about 10% to about 60% by weight, preferably about 10% to about 30% in a gel and about 25% to about 60% in a paste.

Toothpastes as well as gel dentifrices typically contain a natural or synthetic thickener or gelling agent in proportions of about 0.1 to about 10% by weight, preferably about 0.5 to about 5% by weight. Suitable thickeners or gelling agents include Irish moss, iota-carrageenan, kappa-carrageenan, gum tragacanth, starch, polyvinylpyrrolidone, hydroxyethyl propyl cellulose, hydroxybutyl methyl cellulose, hydroxypropyl methyl cellulose, hydroxyethyl cellulose and sodium carboxymethyl cellulose.

In the aspect of the present invention wherein the oral composition is substantially liquid in character such as a mouthwash or rinse, the vehicle is typically a water-alcohol mixture. Generally, the weight ratio of water to alcohol is in the range of from about 3:1 to 10:1 and preferably about 4:1 to about 6:1. The alcohol is a non-toxic alcohol such as ethanol or isopropanol. A humectant such as glycerine, sorbitol or an alkylene glycol such as polyethylene glycol or preferably propylene glycol may be present in amount of about 10–30% by weight. Mouthrinses typically contain about 50–85% of water, about 0 to 20% by weight of a non-toxic alcohol and about 10–40% by weight of the humectant.

Surfactants are used in the compositions of the present invention to achieve increased prophylactic action and assist in achieving thorough and complete dispersion of the 4-alkoxy substituted 2-hydroxybenzophenone antibacterial agent throughout the oral cavity. The surfactant material is preferably anionic, suitable examples which include water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals and alkoyl taurines, and the like. Examples of the last mentioned amides and taurates are N-lauroyl sarcosine, and the sodium, potassium and ethanolamine salts of N-lauroyl, N-myristoyl, or N-palmitoyl sarcosine which should be substantially free from soap or similar higher fatty acid material as well as N-methyl-N-cocoyl (or oleoyl or palmitoyl) taurines.

Any suitable flavoring or sweetening material may also be employed. Examples of suitable flavoring constituents are flavoring oils, e.g. oil of spearmint, peppermint, wintergreen, sassafras, clove, sage, eucalyptus, cinnamon, lemon, and orange, and methyl salicylate. Suitable sweetening agents include sucrose, lactose, maltose, xylitol, sodium cyclamate, perillartine, aspartyl phenyl alanine methyl ester, saccharine and the like. Suitably, flavor and sweetening agents may each or together comprise from about 0.1% to 5% or more of the preparation.

Antitartar agents such as sodium tripolyphosphate, tetrapotassium or tetrasodium pyrophosphate, or mixtures thereof, can be present in the oral compositions of the present invention at concentrations from about 0.5 to about 8% by weight.

Agents used to diminish teeth sensitivity such as potassium chloride, potassium nitrate and potassium citrate can also be included in oral compositions of the present invention at concentrations of about 0.1 to about 10% by weight.

Various other materials may be incorporated in oral compositions of this invention including preservatives, such as sodium benzoate, vitamins and chlorophyll compounds. These adjuvants, when present, are incorporated in the compositions in amounts which do not substantially adversely affect the properties and characteristics desired.

The oral compositions of the present invention may be prepared by suitably mixing the ingredients. For instance, in the preparation of a mouthrinse, the noncationic halogenated hydroxyphenyl ether and hydrogenated lupulone antibacterial agent combination is dispersed in a mixture of ingredients, e.g. alcohol, humectants, surfactants, and flavor are then added and mixed. The ingredients are then mixed under vacuum for about 15–30 minutes. The resulting rinse product is then packaged. Dentifrices are prepared similarly, additional thickener and polishing agents being included in the last or penultimate step.

The antibacterial combination of this invention can be incorporated in lozenges, or in chewing gum or other products, e.g. by stirring into a warm gum base or coating the outer surface of a gum base, illustrative of which may be mentioned include jelutone, rubber latex and vinylite resins desirably with conventional plasticizers or softeners, sugar or other sweeteners or carbohydrates such as glucose, sorbitol and the like.

The vehicle or carrier in a tablet or lozenge is a non-cariogenic solid water-soluble polyhydric alcohol (polyol) such as mannitol, xylitol, sorbitol, malitol, a hydrogenated starch hydrozylate, hydrogenated glucose, hydrogenated disaccharides or hydrogenated polysaccharides, in an amount of about 90 to 98% by weight of the total composition. Salts such as sodium bicarbonate, sodium chloride, potassium bicarbonate or potassium chloride may totally or partially replace the polyol carrier. Tableting lubricants, in minor amounts of about 0.1 to 5% by weight, may be incorporated into the tablet or lozenge formulation to facilitate the preparation of both the tablets and lozenges. Suitable lubricants include vegetable oils such as coconut oil, magnesium stearate, aluminum stearate, talc, starch and Carbowax.

Lozenge formulations contain about 2% gum as a barrier agent to provide a shiny surface as opposed to a tablet which has a smooth finish. Suitable non-cariogenic gums include kappa carrageenan, carboxymethyl cellulose, hydroxyethyl cellulose and the like.

The lozenge or tablet may optionally be coated with a coating material such as waxes, shellac, carboxymethyl cellulose, polyethylene/maleic anhydride copolymer or kappa-carrageenan to further increase the time it takes the tablet or lozenge to dissolve in the mouth. The uncoated tablet or lozenge is slow dissolving, providing a sustained release rate of active ingredients of about 3 to 5 minutes. Accordingly, the solid dose tablet and lozenge composition of this invention affords a relatively longer time period of contact of the teeth in the oral cavity with the active ingredients.

For topical administration of the epidermis, the antibacterial combination of noncationic halogenated hydroxydiphenyl ether and hydrogenated lupulone may be formulated as ointments, creams or lotions. Ointments and creams may, for example, may be formulated with an aqueous or oily base with the addition of suitable thickening and/or gelling agents. Lotions may be formatted with an aqueous or oily base and will in general also contain one or more emulsifying agents, stabilizing agents, dispersing agents, suspending agents or coloring agents.

The following Example further illustrates the present invention, but it is understood that the invention is not limited thereto. All amounts and proportions referred to herein and in the appended claims are by weight unless otherwise indicated.

EXAMPLE

The ingredients of a rinse formulation (Composition A) containing both Triclosan and a mixture of hydrogenated lupulones, hexahydrolupulone and hexahydrocolupulone hereinafter referred to as "HHBA" was prepared and the ingredients for Composition A are listed in Table I below. For purposes of comparisons, the same rinse formulation was prepared in which either Triclosan or HHBA was absent as well as a placebo in which neither compound was present.

The ingredients of these comparative compositions are also listed in Table I below.

TABLE I

| | Composition | | | |
|---|---|---|---|---|
| | A | B | C | D |
| Ingredient Name | Weight Percent | | | |
| Deionized water - irradiated | 48.940 | 48.970 | 48.970 | 49.000 |
| Glycerin (99.5%) | 10.000 | 10.000 | 10.000 | 10.000 |
| Sorbitol (70% soln.) | 10.000 | 10.000 | 10.000 | 10.000 |
| Propylene glycol | 15.000 | 15.000 | 15.000 | 15.000 |
| Ethanol (96%) | 15.000 | 15.000 | 15.000 | 15.000 |
| Sodium lauryl sulfate | 0.250 | 0.250 | 0.250 | 0.250 |
| Pluronic F-127 | 0.250 | 0.250 | 0.250 | 0.250 |
| Sodium methyl cocoyl taurate (95%) | 0.250 | 0.250 | 0.250 | 0.250 |
| Flavor | 0.100 | 0.100 | 0.100 | 0.100 |
| Potassium hydroxide (45% soln.) | 1.050 | 0.050 | 0.050 | 0.050 |
| Dibasic potassium phosphate | 0.100 | 0.100 | 0.100 | 0.100 |
| Triclosan | 0.030 | 0.030 | — | — |
| HHBA* (96% purity) | 0.030 | — | 0.030 | — |
| Total Ingredients | 100.000 | 100.000 | 100.000 | 100.000 |

*A mixture of hexahydroluplone (35% by weight) and hexahydrocolupulone (65% by weight)

The rinse compositions listed in Table I were tested using a microbiological assay namely, Minimum Inhibitory Concentration (MIC) and bacterial growth inhibition on hydroxyapatite disks.

The gram-positive oral bacterium *Actinomyces viscosus* was routinely grown overnight in trypticase soy broth (Difco Labs, Detroit, Mich.) at 37° C. A gram stain of the cultures was prepared to determine the purity of the cultures prior to in vitro testing of the rinse compositions.

MIC Assay

The bacterial strain grown for 18 hours at 37° C. in trypticase soy broth (TSB) was diluted in fresh broth to adjust its optical density between 0.1 and 0.2 absorption units at 610 nm prior to MIC determinations.

The MIC of the rinse solution was diluted in TSB and was determined using the microtiter format according to standard procedures (Manual of Clinical Microbiology, 1995). The results are recorded in Table II below.

Bacterial Growth Inhibition Assay on Hydroxyapatite Disks

The antiplaque effect of the rinses were assessed by a growth inhibition test with A. viscosus using hydroxyapatite disks which were treated with the rinse and bacterial growth monitored by measuring optical density at 610 nm after 2 hours and 24 hours after treatment of the disks. In this test, the hydroxyapatite disk was placed in a test tube containing clarified human saliva and incubated overnight at 37° C. Thereafter, the saliva was removed from the tube and replaced with rinse solution and incubated for 0.75 hours at 37° C. whereupon the disk was placed in a transparent plastic tube containing bacterial strains diluted in TSB to an OD of 0.2 at 610 nm. The results of the microbiological assays are recorded in Tables II below.

TABLE II

| Rinse Composition | MIC as a function of % rinse concentration for bacterial inhibition | MIC as a function of active concentration (in ppm) |
| --- | --- | --- |
| A | 0.0488 | 0.29 |
| B | 0.19 | 1.17 |
| C | 0.39 | 2.3 |
| D | 1.56 | — |

Although the MIC results recorded in Table II indicate that the HHBA rinse (Composition C) was active against A. viscosus, the rinse composition containing both Triclosan and HBBA (Composition A) provided a MIC that was 5 to 10 times less than rinses which contained only Triclosan or HHBA alone (Compositions B and C).

TABLE III

| Rinse Composition | Bacterial OD at 2 hrs. | Bacterial OD at 24 hrs. |
| --- | --- | --- |
| A | 0.27 | 0.27 |
| B | 0.6 | 1.38 |
| C | 0.3 | 0.5 |
| D | 1.52 | 1.35 |

The results recorded in Table III indicate that the rinse Composition A containing both HHBA and Triclosan provided better antibacterial activity than rinses with either Triclosan or HHBA alone after 2 hours and 24 hours post-treatment.

A determination of factional inhibitory concentration (FIC) value from the results recorded in Table II indicate antibacterial synergistic activity resulting form the combination of Triclosan and HHBA.

FIC value (fractional inhibitory concentration) is used to indicate the synergistic activities and is described in L. B. Quesnel, A. R. Al-Naijar and P. Buddhavudhikrai in Journal of Applied Bacteriology, 1978, vol. 45, pages 397–405, L. O. Garrod, H. P. Lambert, F. O'Grady and P. M. Waterworth in Antibiotic and Chemotherapy, pages 282–286 and 514–518.

$$FIC = \frac{MIC \text{ of Triclosan in mixture}}{MIC \text{ of Triclosan alone}} + \frac{MIC \text{ of HHBA in mixture}}{MIC \text{ of HHBA alone}}$$

| FIC | Implies |
| --- | --- |
| ≤ 0.7 | Synergism |
| 1 + /−0.3 | Additive |
| ≥ 1.3 | Antagonistic |

Based on this formula, the FIC of Triclosan+HHBA is 0.373 indicating the combination shows a synergistic effect as an antibacterial mixture.

What is claimed is:

1. An oral antiplaque composition comprising an orally acceptable vehicle and an effective antiplaque amount of a synergistic combination of about 0.003 to about 2.0% by weight Triclosan and about 0.003 to about 2.0% by weight of a mixture of hexahydrocolupulone and hexahydrolupulone.

2. The composition of claim 1 wherein nonionic halogenated diphenyl ether is present in the oral composition in an amount in the range of about 0.003 to about 2.0% by weight.

3. The composition of claim 1 wherein the hydrogenated lupulone is present in the composition in an amount in the range of about 0.003 to about 2.0% by weight.

4. An antibacterial composition comprising an effective amount of a combination of a noncationic halogenated hydroxydiphenyl ether and a hydrogenated lupulone.

5. The composition of claim 4 wherein the noncationic halogenated diphenyl ether compound is Triclosan.

6. The composition of claim 4 wherein the hydrogenated lupulone is hexahydrolupulone.

7. The composition of claim 4 wherein the hydrogenated lupulone acid is hexahydrocolupulone.

8. The composition of claim 4 wherein the hydrogenated lupulone is a mixture of hexahydrolupulone and hexahydrocolupulone.

9. A method comprising inhibiting the growth of gram-positive bacteria by contacting the bacteria with a composition comprising a pharmaceutically acceptable vehicle and an effective antibacterial amount of a synergistic combination of about 0.003 to about 2% by weight of Triclosan and about 0.003 to about 2% by weight of a mixture of hexahydrocolupulone and hexahydrolupulone.

10. The method of claim 9 wherein nonionic halogenated diphenyl ether is present in the vehicle in an amount in the range of about 0.003 to about 2.0% by weight.

11. The method of claim 9 wherein the hydrogenated lupulone is present I the vehicle in an amount in the range of about 0.003 to about 2.0% by weight.

* * * * *